(12) United States Patent
Kawaguchi et al.

(10) Patent No.: US 12,013,056 B2
(45) Date of Patent: Jun. 18, 2024

(54) CLAMP

(71) Applicant: TERUMO KABUSHIKI KAISHA, Tokyo (JP)

(72) Inventors: Satoshi Kawaguchi, Shizuoka (JP); Masahiro Akiyama, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 44 days.

(21) Appl. No.: 17/970,324

(22) Filed: Oct. 20, 2022

(65) Prior Publication Data

US 2023/0037423 A1 Feb. 9, 2023

Related U.S. Application Data

(63) Continuation of application No. PCT/JP2021/017190, filed on Apr. 30, 2021.

(30) Foreign Application Priority Data

May 11, 2020 (JP) .................................. 2020-083048

(51) Int. Cl.
*F16K 7/06* (2006.01)
*A61M 5/168* (2006.01)
*A61M 39/28* (2006.01)

(52) U.S. Cl.
CPC ........... *F16K 7/063* (2013.01); *A61M 39/284* (2013.01); *A61M 5/16813* (2013.01)

(58) Field of Classification Search
CPC .. A61M 39/28; A61M 39/284; A61M 39/281; A61M 39/283; A61M 39/285;
(Continued)

(56) References Cited

U.S. PATENT DOCUMENTS 4,346,869 A * 8/1982 MacNeill ............ A61M 39/284
251/10
4,429,852 A * 2/1984 Tersteegen .......... A61M 39/284
604/533
(Continued)

FOREIGN PATENT DOCUMENTS

EP 0637456 A1 2/1995
FR 3093928 A1 9/2020
(Continued)

OTHER PUBLICATIONS

International Preliminary Report on Patentability for International Application No. PCT/JP2021/017190, mailed Nov. 24, 2022.
(Continued)

*Primary Examiner* — Kevin F Murphy
*Assistant Examiner* — Jonathan J. Waddy
(74) *Attorney, Agent, or Firm* — Sheridan Ross, PC

(57) ABSTRACT

A clamp includes a fixed portion on which a medical tube is placed, a movable portion that is provided above the fixed portion to face the fixed portion, and a closing portion that presses and closes the medical tube when the movable portion is pressed toward the fixed portion. The closing portion includes a presser that protrudes from the movable portion toward the fixed portion and presses the medical tube, a pair of sidewalls that extends, like a wall, from both sides of the fixed portion and prevents the medical tube from being shifted laterally, and a guide structure that allows the presser to be guided between the sidewalls.

12 Claims, 10 Drawing Sheets

(58) Field of Classification Search
CPC .............. A61M 39/286; A61M 39/287; A61M 5/16813; F16K 7/06; F16K 7/063; F16K 7/061; F16K 7/065; F16K 7/066; F16K 7/068
USPC ...................................................... 251/9, 10
See application file for complete search history.

(56) References Cited

U.S. PATENT DOCUMENTS

| | | | |
|---|---|---|---|
| 6,234,448 B1* | 5/2001 | Porat ................... | A61M 39/284 251/9 |
| 2012/0035553 A1* | 2/2012 | Lombardo .......... | A61M 39/284 604/250 |
| 2013/0310768 A1 | 11/2013 | Ebara et al. | |
| 2017/0120038 A1 | 5/2017 | Tsukamoto et al. | |
| 2017/0120040 A1* | 5/2017 | Burkholz ............ | A61M 39/288 |
| 2017/0254423 A1* | 9/2017 | Mueller ................. | F16K 7/061 |
| 2018/0104467 A1* | 4/2018 | Kato ...................... | A61M 39/28 |
| 2019/0030315 A1 | 1/2019 | Fiege et al. | |
| 2019/0314031 A1* | 10/2019 | Thomas ............... | A61B 17/122 |

FOREIGN PATENT DOCUMENTS

| | | |
|---|---|---|
| JP | 2018-000836 A | 1/2018 |
| WO | WO 2012/111310 A1 | 8/2012 |
| WO | WO 2016/002487 A1 | 1/2016 |

OTHER PUBLICATIONS

European Search Report for corresponding European Application No. 21803956.8, mailed Aug. 4, 2023.
International Search Report for International Application No. PCT/JP2021/017190, mailed Jul. 6, 2021.
Written Opinion for International Application No. PCT/JP2021/017190, mailed Jul. 6, 2021.

* cited by examiner

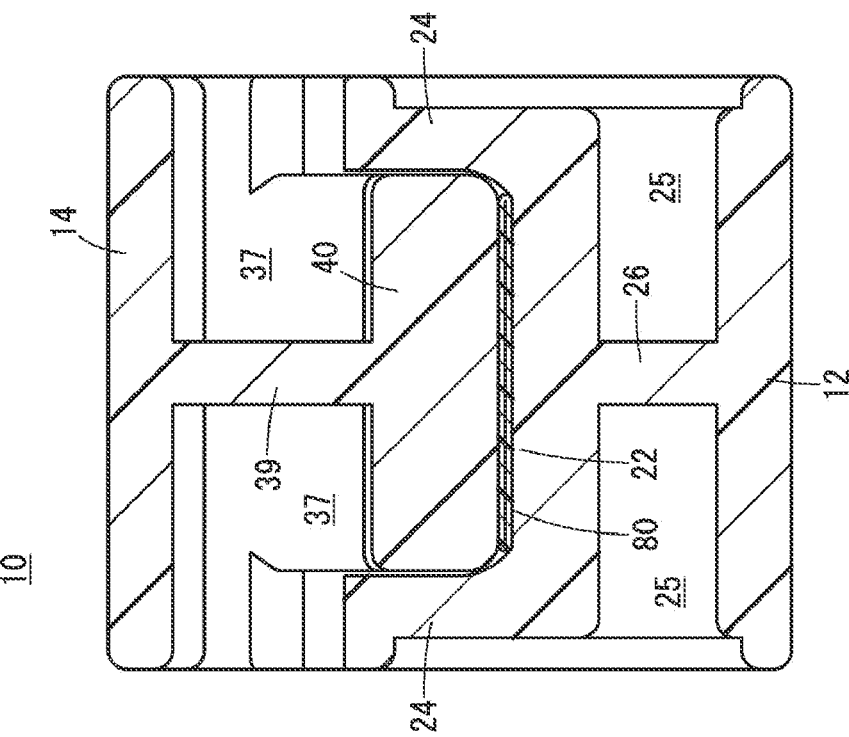
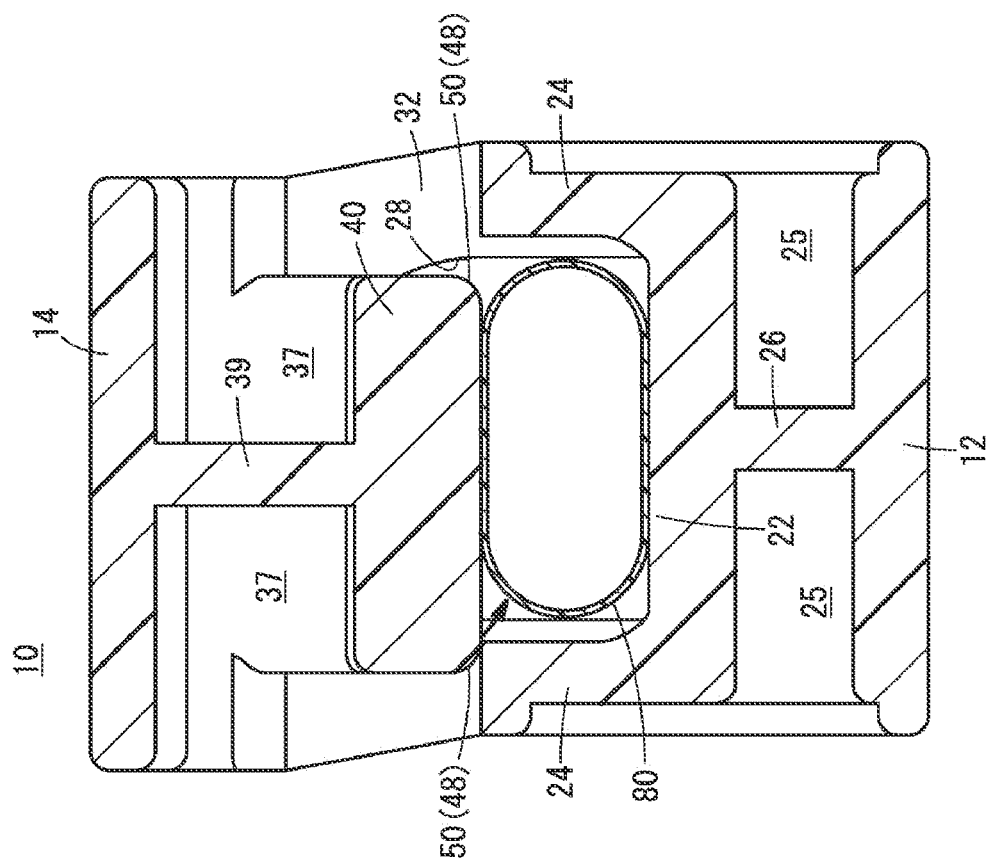

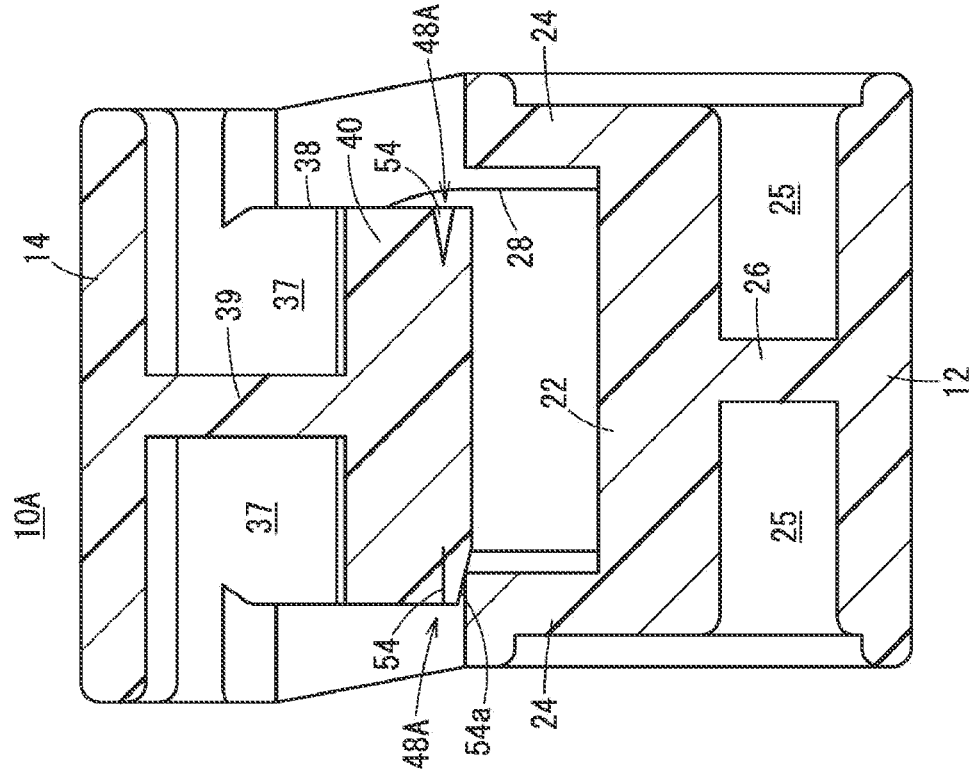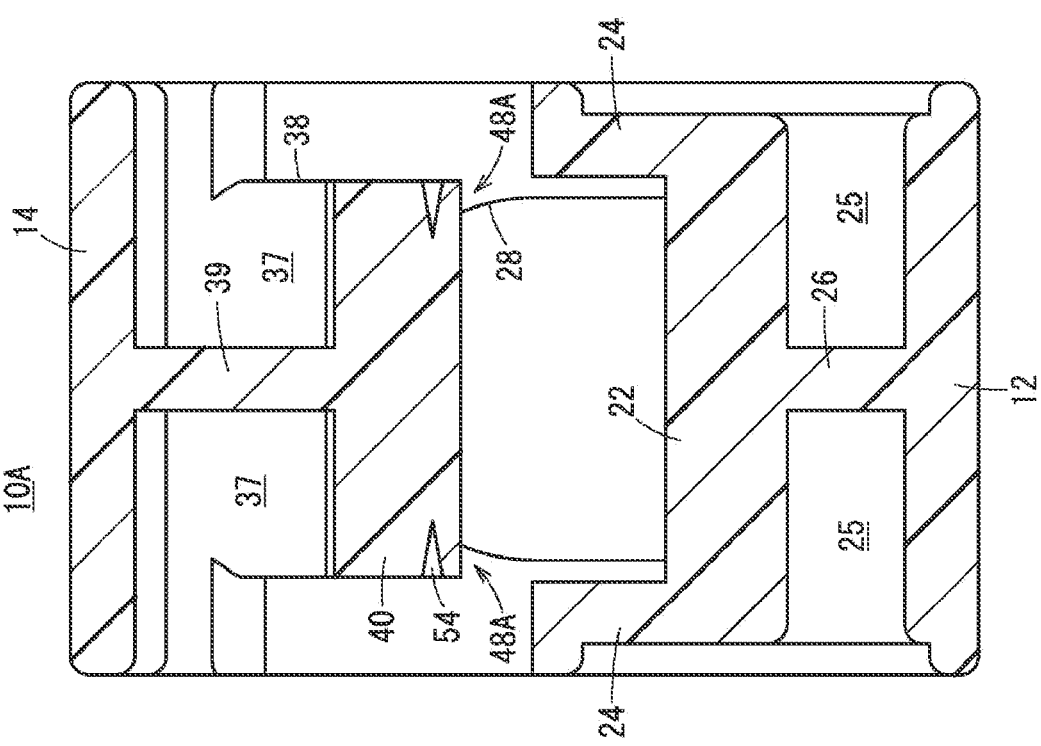

CLAMP

CROSS-REFERENCE TO RELATED APPLICATIONS

The present disclosure is a continuation of and claims benefit to PCT/JP2021/017190 filed on Apr. 30, 2021, entitled "CLAMP" which claims priority to Japanese Patent Application No. 2020-083048 filed on May 11, 2020. The entire disclosure of the applications listed above are hereby incorporated herein by reference, in their entireties, for all that they teach and for all purposes.

BACKGROUND

The present disclosure relates to a clamp for closing a tube having flexibility.

A flexible medical tube is used as a flow path connecting blood bags of a blood collection set or the like, and a flow path connecting bags of a transfusion set or the like, and a clamp for closing the flow path is attached to the medical tube.

The clamp is provided with a hole through which the medical tube is inserted, a presser that presses and closes the inserted medical tube, a movable portion for applying an operation force to the presser, and a lock mechanism that keeps the movable portion in a pressed state. In the initial state of the clamp, the presser is open because of a resilient force of the movable portion. In a case where a user presses the movable portion, the presser presses and closes the tube, and the movable portion is locked by the lock mechanism, which keeps the tube closed by the presser.

Meanwhile, in a blood center or the like to process a large number of blood bags, a user sometimes performs an operation for closing many clamps continuously. Further, in a busy medical setting, a user sometimes performs an operation for quickly closing a clamp. In such cases, the user may operate the clamp with one hand without visually checking the operation. In a rare case, in the clamp, the medical tube is pressed in a state of being laterally shifted from the presser, so that the flow path may be incompletely closed.

In order to prevent the flow path of the medical tube from being closed incompletely, JP 2018-000836 A discloses a technique in which a pair of sidewalls is provided on both sides of a presser to prevent the medical tube from being shifted laterally.

BRIEF SUMMARY

However, in the clamp described above, it has been found that a new problem occurs in which the movable portion is locked by the lock mechanism with the presser overlying the sidewall and the presser sometimes does not close the medical tube completely.

In light of the above, an object of the present disclosure is to provide a clamp capable of reliably closing a medical tube.

One aspect of the following disclosure is a clamp including a fixed portion on which a tube is placed; a movable portion that is provided above the fixed portion to face the fixed portion; and a closing portion configured to press and close the tube in response to the movable portion pressed toward the fixed portion, in which the closing portion includes a presser that protrudes from the movable portion toward the fixed portion and presses the tube, a pair of sidewalls that extends in a wall shape from both sides of the fixed portion and prevents the tube from being shifted laterally, and a guide structure that is provided in at least one of the presser and the sidewall and allows the presser to be guided between the sidewalls.

According to the clamp from the above viewpoint, even in a case where the presser overlies the sidewall (e.g., where the presser is laterally shifted, or misaligned, in the width direction relative to the fixed portion, etc.), the guide structure guides the presser (e.g., by centering the presser relative to the fixed portion) toward the inside of the sidewall, so that the medical tube can be reliably closed.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages are described herein and will be apparent to those skilled in the art upon consideration of the following Detailed Description and in view of the figures.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 6A is a cross-sectional view illustrating an operation for a case where a presser overlies a sidewall in the clamp illustrated in FIG. 1;

FIG. 6B is a cross-sectional view illustrating a closed state of a medical tube by the clamp shown in FIG. 6A;

FIG. 7A illustrates a cross-sectional view of a clamp according to at least one embodiment of the present disclosure;

FIG. 7B is a cross-sectional view illustrating an operation for a case where a presser of the clamp of FIG. 7A overlies a sidewall;

DETAILED DESCRIPTION

Figure 1:
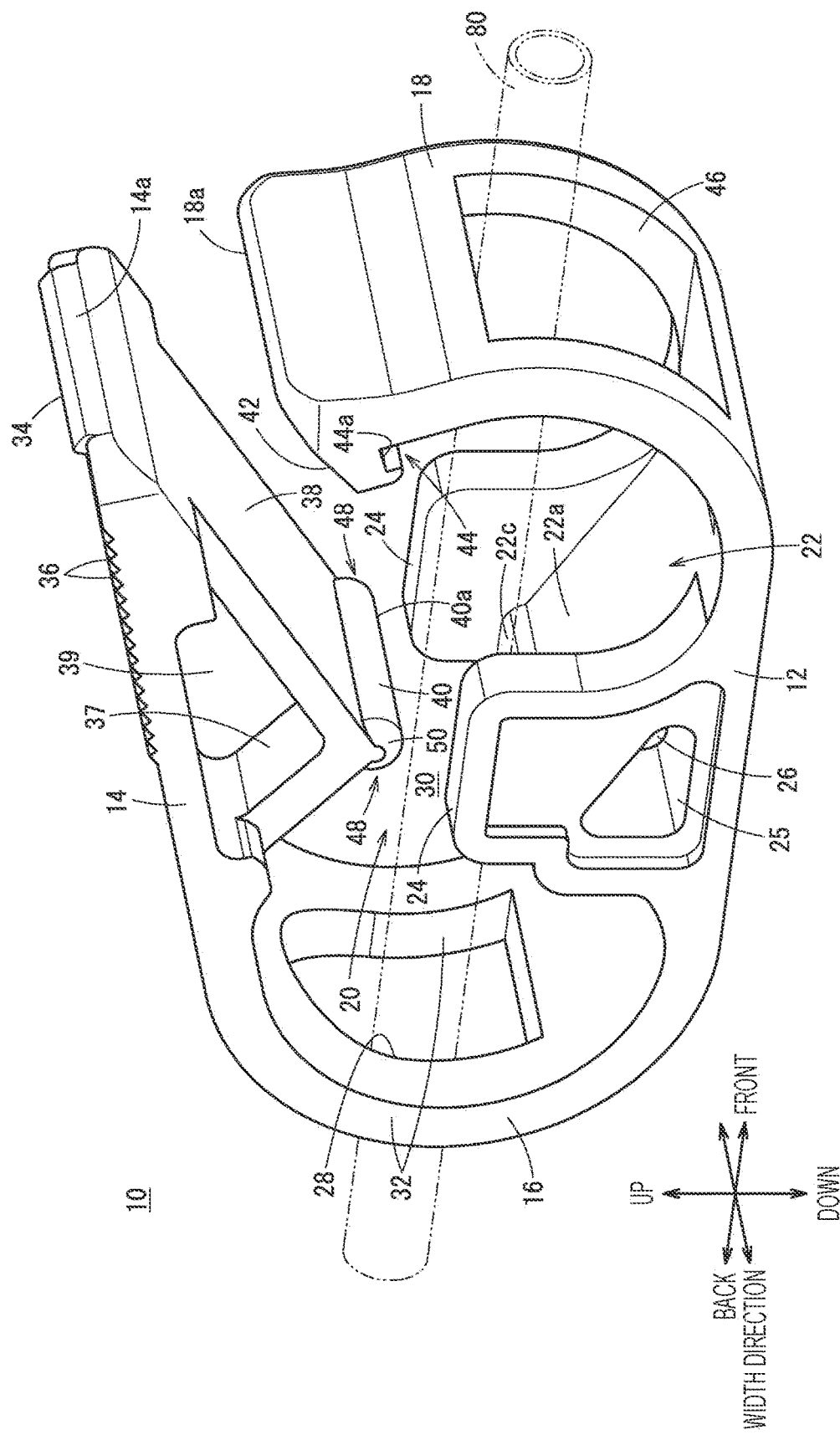
FIG. 1 illustrates a first perspective view of a clamp according to at least one embodiment of the present disclosure.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims.

It is with respect to the above issues and other problems that the embodiments presented herein were contemplated.

Hereinafter, embodiments of a clamp will be described in detail with reference to the accompanying drawings.

FIG. 1 illustrates a clamp 10 according to at least one embodiment of the present disclosure. The clamp 10, which may be integrally formed of a resin material, may be selectively engaged with, or attached to, a medical tube 80, such as a blood tube or an infusion tube, and may be used for an operation of selectively closing and/or opening the medical tube 80. Stated another way, the clamp 10 may be used to selectively open and/or close a flow path of a medical tube 80. As illustrated in FIG. 1, the clamp 10 includes a fixed portion 12 on which the medical tube 80 is placed or introduced, a movable portion 14 (e.g., clamp arm) provided above the fixed portion 12 to face the fixed portion 12, a curved portion 16 connecting the fixed portion 12 and the movable portion 14 to each other, an upright portion 18 facing the curved portion 16, and a closing portion 20 for closing the medical tube 80.

The fixed portion 12 may correspond to a plate-like portion extending along a plane arranged in the fore-aft (e.g., front-back) direction. The medical tube 80 may be placed on an upper part of the fixed portion 12. The curved portion 16 of the clamp 10 may extend upward from a rear, or back, end of the fixed portion 12. The upright portion 18 extends upward from a front end of the fixed portion 12. At a central part of the fixed portion 12 in the fore-aft direction, a base 22 constituting a part of the closing portion 20 and a pair of sidewalls 24 extending upward from both sides of the fixed portion 12 in the width direction are formed. In some embodiments, the clamp 10 and/or one or more components of the clamp 10 may be symmetrical about a plane that passes through a center of the clamp 10 in the width direction, from the front of the clamp 10 to the back of the clamp 10.

The curved portion 16 is a member extending upward from the fixed portion 12, and is curved in a semicircular shape when viewed from the side. The curved portion 16 can be elastically deformed in a direction of reducing or increasing the radius of curvature. In some embodiments, the curved portion 16 may correspond to a living hinge of the clamp 10 that is capable of being elastically deformed. The curved portion 16 has, on its central part, a first insertion hole 28, or first aperture, that penetrates, or passes, through the curved portion 16 in the thickness direction (fore-aft direction). The first insertion hole 28 is a hole, or aperture, through which the medical tube 80 may be introduced into a tube arrangement space 30 (e.g., a tube receiving space, etc.) disposed between the fixed portion 12 and the movable portion 14. The first insertion hole 28 is formed to have dimensions in the width direction and the up-down direction that allows the medical tube 80 to be inserted thereinto. A column portion 32 is formed on either side portion of the first insertion hole 28. The hardness (e.g., spring constant) at the time of elastic deformation of the curved portion 16 is based on the elasticity of the pair of column portions 32 that are disposed on either side portion of the first insertion hole 28.

An upper end of the curved portion 16 is integrally connected to a rear end of the movable portion 14. The curved portion 16 may be elastically deformed, so that the movable portion 14 pivots about a rear end of the curved portion 16, which allows the movable portion 14 to be displaced in the up-down direction of the fixed portion 12. The movable portion 14 may be pressed, displaced, or otherwise moved, from an open state of the clamp 10 (e.g., an unclamped state) to a closed state of the clamp 10 (e.g., a clamped state). In moving from the open state of the clamp 10 to the closed state of the clamp 10, a pressing force may be applied to the movable portion 14 moving the movable portion 14 in a direction toward the fixed portion 12 of the clamp 10 (e.g., moving against a spring force that is provided by the curved portion 16 or the pair of column portions 32, etc.). In some embodiments, the clamp 10 may be moved from the closed state of the clamp 10 to the open state of the clamp 10 by releasing the pressing force from the movable portion 14 and allowing the spring force of the curved portion 16 to move the movable portion in a direction away from the fixed portion 12. In the open state, the movable portion 14 may be arranged spaced apart a first distance from the fixed portion 12 of the clamp 10. In the closed state, the movable portion 14 may be arranged a second distance from the fixed portion 12 (e.g., such that the movable portion is arranged closer to, or in contact with, the fixed portion 12). In any event, the second distance is smaller than the first distance.

Figure 2:
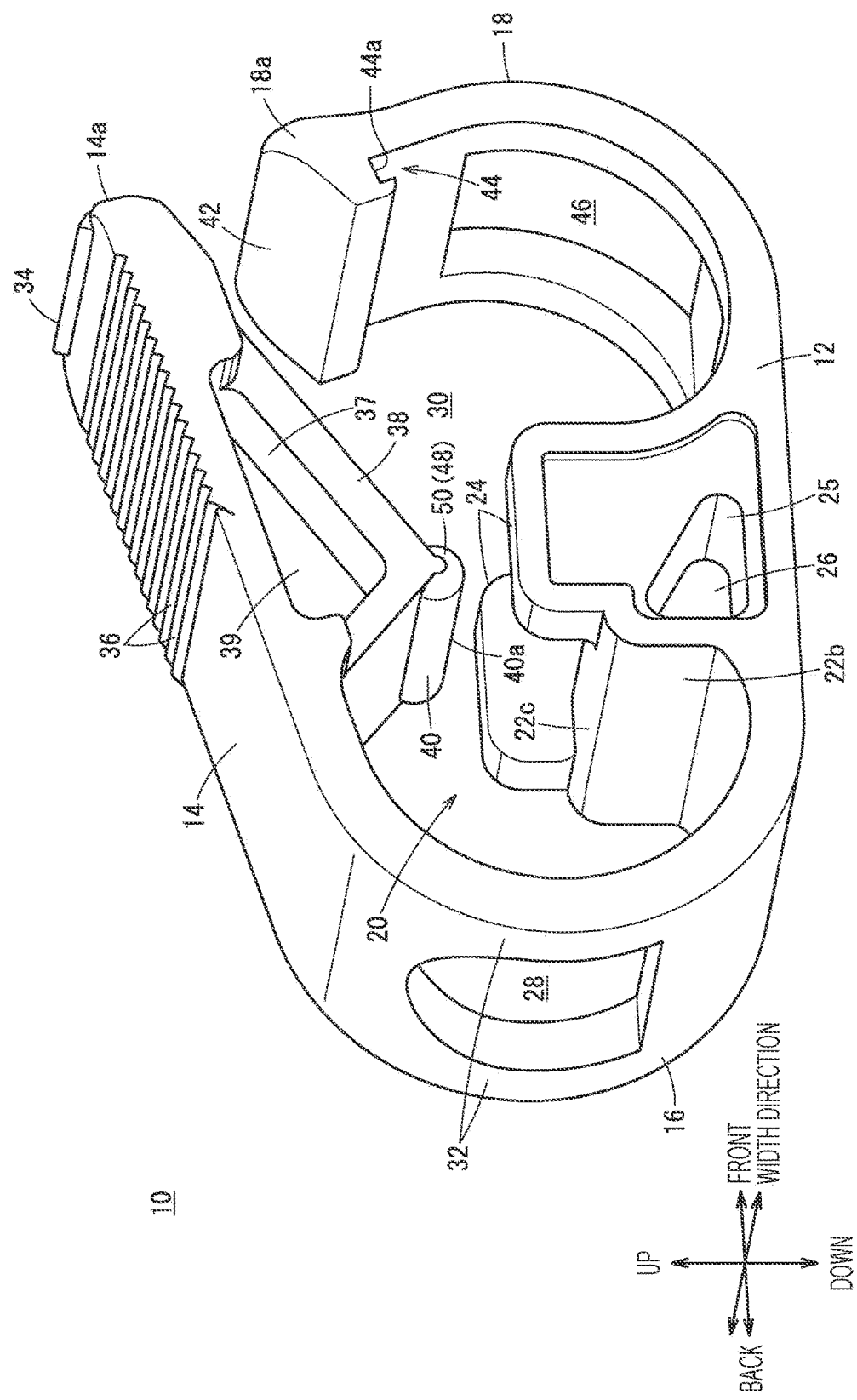
FIG. 2 illustrates a second perspective view of the clamp according to at least one embodiment of the present disclosure.

The movable portion 14 is a plate-like member, and a distal end 14a thereof is provided above the front end of the fixed portion 12. A claw 34, or protrusion, for engaging with a lock mechanism 44, described later, is formed on the upper side of the distal end 14a of the movable portion 14. In some embodiments, the claw 34 is formed to extend linearly in the width direction. As illustrated in FIG. 2, a plurality of ridges 36 including linear protrusions extending in the width direction is provided on the upper surface of the movable portion 14. The ridges 36 function as non-slip portions when a user applies an operation force (e.g., a pressing force, etc.) to the movable portion 14.

The movable portion 14 has, on its lower side, a protrusion 38 and a presser 40 (e.g., a press bar, contact protrusion, etc.) constituting a part of the closing portion 20. Details of the protrusion 38 and the presser 40 are described later with reference to the description of the closing portion 20.

The upright portion 18 extends upward from the front end of the fixed portion 12. The upright portion 18 extends upward while being curved in an arc shape when viewed from the side. The upright portion 18 comprises an upper end portion 18a in which an inclined surface 42 is arranged facing a lower portion of the distal end 14a of the movable portion 14. A lock mechanism 44 configured to engage with the claw 34 is formed in the upright portion 18 (e.g., underneath the inclined surface, etc.). The inclined surface 42 is formed as a surface that slopes downward from the front of the clamp 10 toward the rear of the clamp 10. In a case where the movable portion 14 is pressed (e.g., in a direction toward the fixed portion 12), the inclined surface 42 abuts on, or contacts, the distal end 14a of the movable portion 14 and slides along the same, and guides the distal end 14a of the movable portion 14 toward the lock mechanism 44. In response to the pressing force from the movable portion 14 acting on the inclined surface 42, the upright portion 18 is curved so as to be pushed forward to spread out. In some embodiments, as the movable portion 14 is pressed into contact with the inclined surface 42 of the upright portion 18, the pressing force may cause the upright portion 18 to hinge outwardly (e.g., away from a center of the clamp 10, etc.) about a pivot point of the upright portion 18. In at least one embodiment, the upright portion 18 may correspond to a living hinge that is capable of being elastically deformed during engagement and disengagement of the claw 34 with the lock mechanism 44, etc. In some embodiments, the movable portion 14 may be hingedly, or pivotally, attached to the fixed portion 12 at the back end of the clamp 10.

The lock mechanism 44 is a hook-shaped portion having a groove 44a that is formed to be recessed upward and that extends in the width direction. In a case where the movable portion 14 is pushed down (e.g., into a clamped state), the lock mechanism 44 may engage with the claw 34 of the distal end 14a preventing the movable portion 14 from returning upward, and locking the movable portion 14 in a state of being pushed downward (e.g., a pressed state). For instance, as the movable portion 14 is pressed in a direction toward the fixed portion 12, the claw 34 may be moved into the groove 44a of the lock mechanism 44. When the claw 34 is disposed in the groove 44a of the lock mechanism 44, the clamp 10 may be referred to as being in a locked state.

The upright portion 18 has a second insertion hole 46, or second aperture, arranged below the lock mechanism 44. The second insertion hole 46 is formed to penetrate, or pass, through the upright portion 18 in the thickness direction (e.g., the fore-aft direction). The second insertion hole 46 may be formed in a rectangular shape when viewed from the front of the clamp 10. The second insertion hole 46 is formed to have dimensions in the width direction and the up-down direction larger than the diameter of the medical tube 80, which allows the medical tube 80 to be inserted into the second insertion hole 46.

As illustrated in FIG. 1, the medical tube 80 is introduced into the tube arrangement space 30 between the fixed portion 12 and the movable portion 14 through the first insertion hole 28 of the curved portion 16 and the second insertion hole 46 of the upright portion 18. In this arrangement, the clamp 10 may be positioned along a length of the medical tube 80 to a desired area of clamping, etc. The medical tube 80 may be selective closed (e.g., restricting flow through the medical tube 80, etc.) by the clamp 10 at a point of the closing portion 20.

Hereinafter, the closing portion 20 is described. As illustrated in FIG. 1, the closing portion 20 includes the base 22 and the sidewalls 24 formed on the fixed portion 12 side, and the protrusion 38 and the presser 40 formed on the movable portion 14 side.

Figure 4:
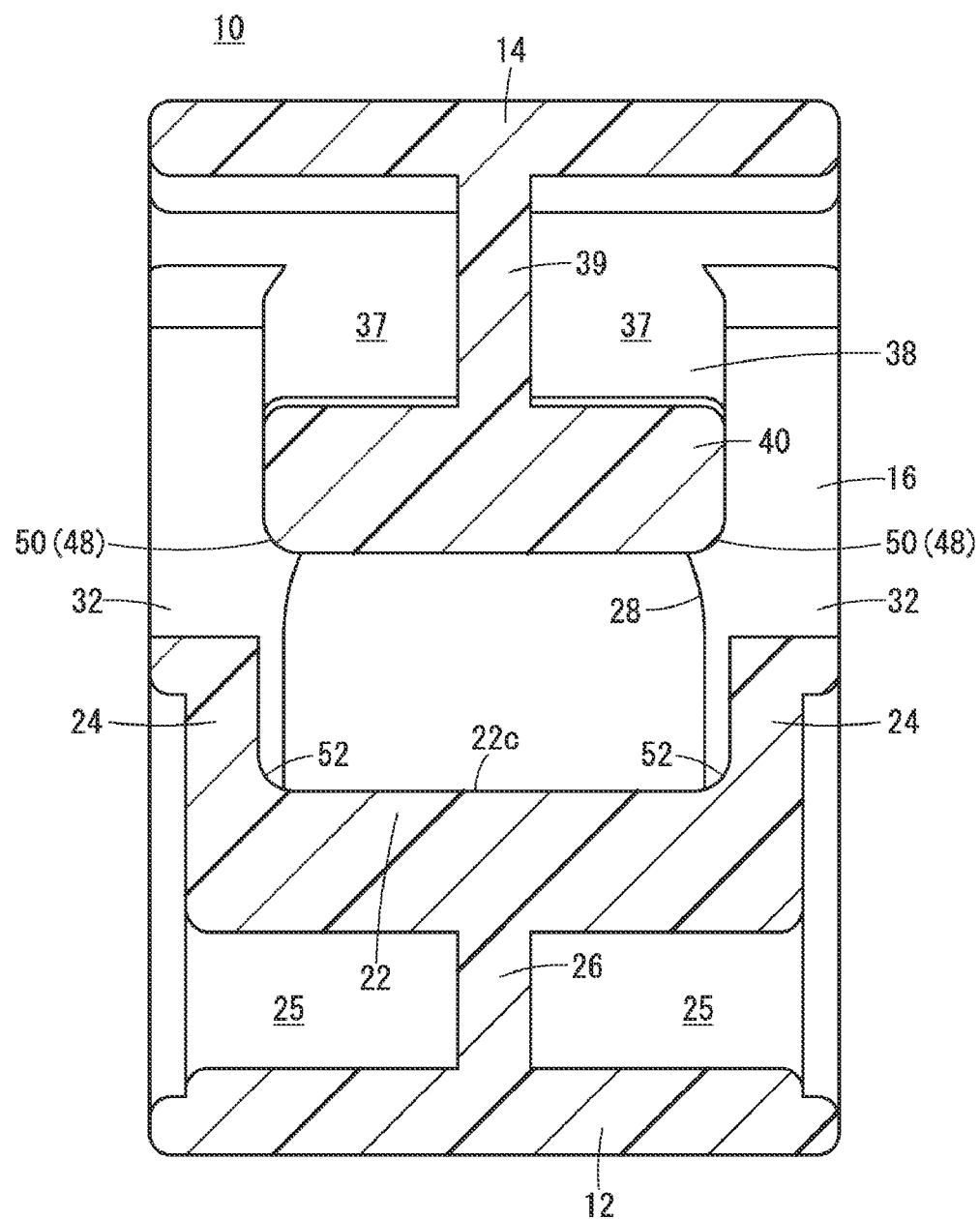
FIG. 4 illustrates a cross-sectional view of the clamp taken along the line IV-IV in FIG. 3.

The base 22 includes a front surface 22a gently inclined, a rear surface 22b extending substantially perpendicular to the fixed portion 12, and an upper end surface 22c that is formed between an upper end of the front surface 22a and an upper end of the rear surface 22b and is parallel to the fixed portion 12, as illustrated in FIG. 2. The upper end surface 22c is formed at a position where the upper end surface 22c can abut on the presser 40, described later, in a case where the movable portion 14 is pressed, and the upper end surface 22c functions as a portion that supports the medical tube 80 from below. Each side portion of the base 22 is hollowed out by a hollow part 25. As illustrated in FIG. 4, the base 22 is supported from below by a rib 26, or web, that is provided at the center of the base 22 and/or the clamp 10 in the width direction. In some embodiments, the upper end surface 22c may be arranged as a flat, or uncurved, surface. For example, the upper end surface 22c may be flat extending along a length in the fore/aft direction and/or in the width direction. In at least one embodiment, a rear radiused surface may be disposed between the rear surface 22b and the upper end surface 22c. Additionally or alternatively, a front radiused surface may be disposed between the front surface 22a and the upper end surface 22c. Among other things, these one or more radiused surfaces may provide a blunt, dull, smooth, or non-sharp edge on one or more sides (e.g., the front side, the back side, and/or the front and back sides) of the upper end surface 22c. The radiused surfaces may prevent creasing, cutting, or damage of a medical tube 80 that is disposed in the closing portion 20 of the clamp 10.

The pair of sidewalls 24 is provided on both sides of the base 22. The sidewalls 24 are formed to extend in a wall shape above the fixed portion 12 along the side portions of the fixed portion 12. The sidewalls 24 protrude upward over the upper end surface 22c to prevent the medical tube 80 from being shifted laterally (e.g., in the width direction) out of the closing portion 20 of the clamp 10.

The protrusion 38 is formed to protrude from the lower surface of the movable portion 14 in a direction toward the fixed portion 12. The protrusion 38 is formed in a triangular shape having a top (e.g., triangle peak portion) on the lower end side when viewed from the side. The protrusion 38 is formed to have a dimension in the width direction smaller than the distance between the pair of sidewalls 24, so that the protrusion 38 can be inserted between the sidewalls 24. Each side portion of the protrusion 38 is hollowed out by a hollow part 37. Further, as illustrated in FIG. 4, the protrusion 38 is supported from the movable portion 14 side above by a rib 39, or web, provided at the center of the protrusion 38 and/or clamp 10 in the width direction. The presser 40 is formed at a lower end of the protrusion 38 (e.g., at the triangle peak portion of the protrusion 38).

The presser 40 is provided above the vicinity of the upper end surface 22c of the base 22 and is provided to protrude from the lower end of the protrusion 38. The presser 40 is formed in a columnar (e.g., bar, cylindrical, arcuate, etc.) shape having a central axis in the width direction, and presses and closes the medical tube 80 through a linear contact portion 40a extending in the width direction. For example, when the presser 40 is configured as having a curved surface (e.g., as a cylinder, bar, etc.), the presser may provide a linear contact region (e.g., line contact zone) extending in the width direction of the clamp 10. The presser 40 is formed to have a dimension in the width direction shorter than a gap between the pair of sidewalls 24 (e.g., providing clearance in the width direction) so that the presser 40 can be inserted between the pair of sidewalls 24. In addition, on both sides of the presser 40 in the width direction, a first inclined structure 48 is formed which is inclined so that the dimension in the width direction of the presser 40 is decreased toward the lower end. In some embodiments, the first inclined structure 48 is configured as a spherical surface 50 (e.g., a domed surface, radiused surface, etc.) as illustrated in FIGS. 1, 2, and 4.

In addition, as illustrated in FIG. 4, a raised portion 52 (e.g., internal radius, fillet, etc.) curved with the same curvature (e.g., radius, diameter, arc size, etc.) as the curvature (e.g., radius, diameter, arc size, etc.) of the spherical surface 50 is formed at a boundary between the upper end surface 22c of the base 22 and the sidewall 24 in order to fill a gap generated when the presser 40 is brought into contact with the upper end surface 22c. The raised portion 52 is formed to extend in the fore-aft direction along bases of the base 22 and the sidewall 24. The raised portion 52 is formed over the entire region of the sidewall 24 in the fore-aft direction. The raised portion 52 is provided to reinforce the sidewall 24. Further, the raised portion 52 can prevent stress from concentrating on the base of the sidewall 24 when an external force acts on the sidewall 24, which can prevent damage to the sidewall 24.

The clamp 10 of the present disclosure is configured as described above, and an operation thereof is described below.

Figure 3:
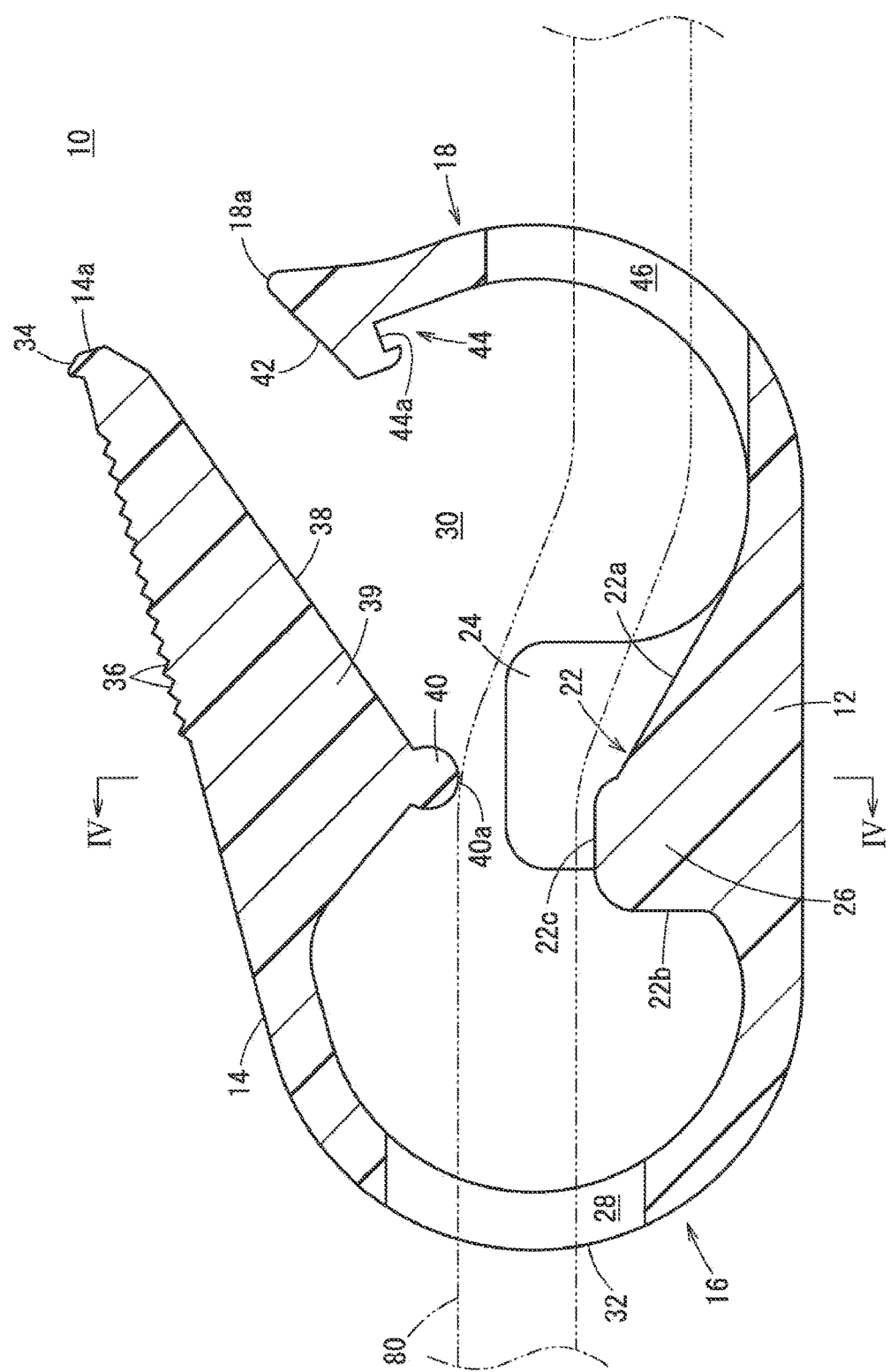
FIG. 3 illustrates a cross-sectional view taken along a center of the clamp in a width direction, as illustrated in FIG. 1.

As illustrated in FIGS. 1 and 3, the clamp 10 is used by inserting the medical tube 80 into the first insertion hole 28 and the second insertion hole 46. The medical tube 80 is placed between the fixed portion 12 and the movable portion 14 as well as between the pair of sidewalls 24, and is held in the tube arrangement space 30.

When the user presses the clamp 10 so that the distal end 14a of the movable portion 14 approaches the fixed portion 12 side, the curved portion 16 is elastically deformed so as to reduce the radius of curvature of the curved portion 16. The movable portion 14 is then displaced so as to approach the fixed portion 12. As illustrated in FIG. 6A, the medical tube 80 is pressed while being sandwiched between the presser 40 and the upper end surface 22c of the base 22. When the movable portion 14 is further pressed, the distal end 14a of the movable portion 14 illustrated in FIG. 1 slides while being in contact with the inclined surface 42 of the upright portion 18. As the movable portion 14 is pushed down, a load in the direction of tilting the upright portion 18 forward acts through the inclined surface 42, and the upper end of the upright portion 18 is deformed so as to tilt forward. The claw 34 of the movable portion 14 is caught by the lock mechanism 44 of the upright portion 18, whereby the movable portion 14 is fixed to the lock mechanism 44.

Since the clamp 10 has, on the curved portion 16, the first insertion hole 28 into which to insert the medical tube 80, the rigidity of the curved portion 16 is low. Therefore, when the user performs an operation of pressing the movable portion 14 (e.g., in a direction toward the fixed portion 12, etc.), the distal end 14a may shift in the width direction and the presser 40 of the movable portion 14 may overlie the sidewall 24 (e.g., as shown in FIG. 6A). In some embodiments, the position of the movable portion 14 overlying, or overlapping, the sidewall 24, or a portion thereof, may be caused by a misalignment of the movable portion 14 relative to the fixed portion 12. This misalignment may be caused by, for instance, a force that is applied to the movable portion that is not perpendicular to the up-down direction, tolerancing of the movable portion 14 relative to the fixed portion 12 of the clamp, warpage and/or damage to a structure of the clamp 10, and/or varying strength (e.g., flexibility, elasticity, etc.) of at least one column portion 32 of the pair of column portions 32 of the clamp 10, etc.

Figure 5:
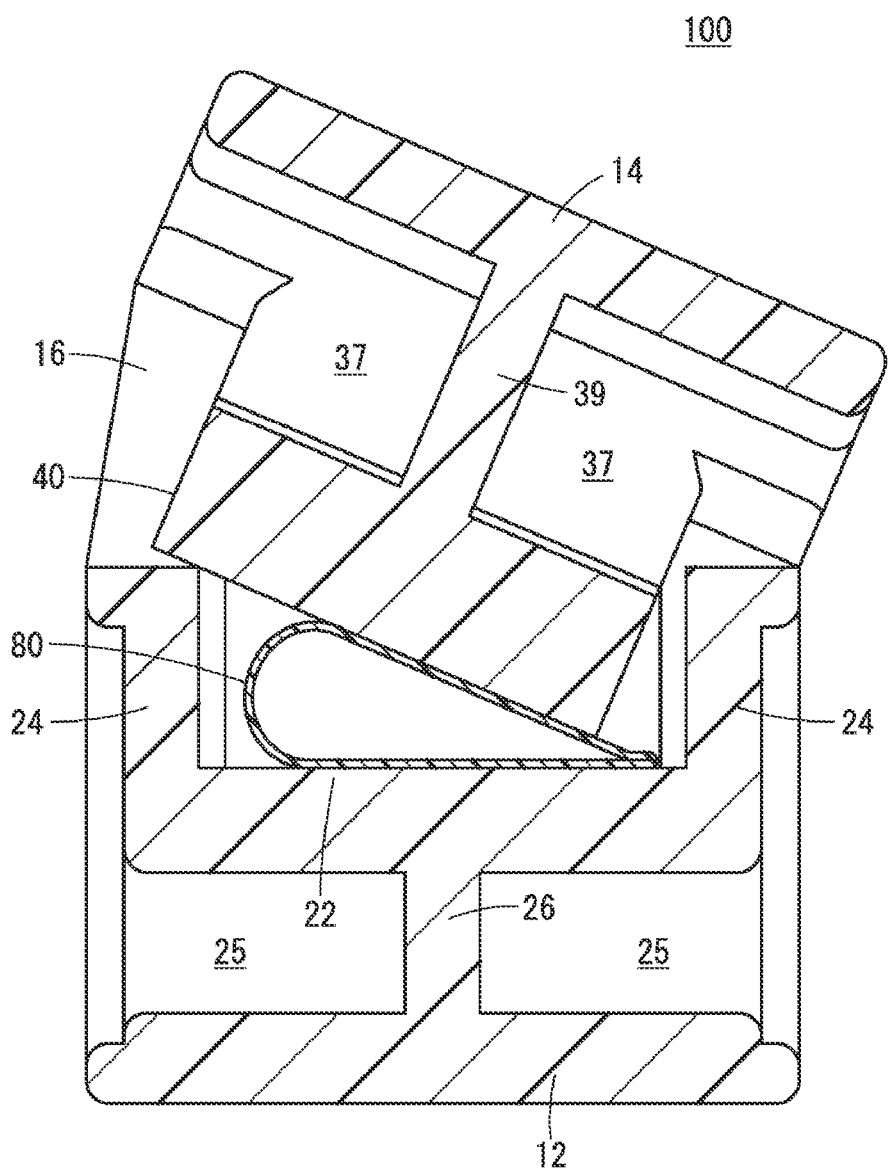
FIG. 5 illustrates a cross-sectional view of an operation example of the clamp according to a comparative example.

A clamp 100 of a comparative example is illustrated in FIG. 5 showing an example in which the first inclined structure 48 is not provided on both sides of the presser 40. In the clamp 100 of the comparative example, in a case where the presser 40 overlies the sidewall 24, that state is maintained. Even in such a case, since the movable portion 14 is formed of a resin material that is elastically deformable, in the clamp 100 of the comparative example, the distal end 14a of the movable portion 14 is fixed to the lock mechanism 44 with the presser 40 overlying the sidewall 24. In this comparative example, even though the clamp 100 is locked, the medical tube 80 is not completely closed. As can be appreciated, this comparative example clamp 100 would still allow fluid to flow through the medical tube 80, even though the comparative example clamp 100 is locked. When used in scenarios where drugs may be administered via the medical tube 80, bodily fluids are flowing through the medical tube 80, and/or the restriction of fluid flow is required to be accurately controlled, an operation of the comparative example clamp 100 may fail, without detection, proving to be unreliable.

In contrast, according to the clamp 10 of the present disclosure, the first inclined structure 48 implemented by the spherical surface 50 is formed on both sides of the presser 40. The first inclined structure 48 is formed to have a curve inclined so that the dimension in the width direction of the presser 40 is decreased toward the lower end. Therefore, even when the presser 40 overlies the sidewall 24, as illustrated in FIG. 6A, the presser 40 is guided between the pair of sidewalls 24 by the first inclined structure 48 as indicated by an arrow. As a result, and according to embodiments of the present disclosure, the clamp 10, as illustrated in FIG. 6B, is structured such that the presser 40 is reliably inserted between the pair of sidewalls 24 and the closing operation of the medical tube 80 can be reliably performed.

In some embodiments, the clamp 10 of the present disclosure has the following effects.

The clamp 10 of the present disclosure includes the fixed portion 12 on which the medical tube 80 (e.g., tube) is placed, the movable portion 14 that is provided above the fixed portion 12 to face the fixed portion 12, and the closing portion 20 that presses and closes the medical tube 80 when the movable portion 14 is pressed toward the fixed portion 12. The closing portion 20 includes the presser 40 that protrudes from the movable portion 14 toward the fixed portion 12 and presses the medical tube 80 with the linear contact portion 40a extending in the width direction, the pair of sidewalls 24 that extends, like a wall, from both sides of the fixed portion 12 and prevents the medical tube 80 from being shifted laterally, and the first inclined structure 48 as a guide structure that is provided in at least one of the presser 40 and the sidewall 24 and allows the presser 40 to be guided, or self-centered, between the sidewalls 24.

According to at least some embodiments of the present disclosure, the clamp 10, even in a case where the presser 40 overlies the sidewall 24, the guide structure guides the presser 40 toward the inside of the sidewall 24, so that the medical tube 80 can be reliably closed.

In the clamp 10, the first inclined structure 48 may be implemented by the spherical surface 50. According to the configuration, the presser 40 can be guided between the pair of sidewalls 24 more smoothly.

In the clamp 10, the raised portion 52, or fillet, corresponding to the shape of the first inclined structure 48 may be formed at the boundary between the fixed portion 12 and the sidewall 24. According to the configuration, since the raised portion 52 can fill the clearance by the first inclined structure 48, the medical tube 80 can be reliably closed.

In the clamp 10, the raised portion 52 may be formed over the entire region of the sidewall 24 along the extending (e.g., longitudinal) direction of the medical tube 80. According to the configuration, the raised portion 52 may increase a rigidity of the sidewall 24, which can prevent stress concentrations, deformation, and/or damage to the sidewall 24.

As described above, an example is described in which the first inclined structure 48 is implemented by the spherical surface 50; however, the present embodiment is not limited thereto, and the first inclined structure 48 may be implemented by a flat inclined surface (e.g., a taper, chamfer, etc.). Alternatively, the first inclined structure 48 may be implemented by connecting a plurality of inclined surfaces having different inclination angles (e.g., multiple tapered surfaces, etc.).

FIG. 7A illustrates a clamp 10A according to at least one embodiment of the present disclosure. In some embodiments, the clamp 10A may be different from the clamp 10 described above and illustrated in FIGS. 1 to 4, 6A, and 6B in a configuration of the first inclined structure 48A of the presser 40. Note that the configuration of the clamp 10A other than the first inclined structure 48A may be similar, if not identical, to that of the clamp 10 described above. In the clamp 10A, components similar, if not identical, to those of the clamp 10 are denoted by the same reference numerals, and the detailed description thereof is omitted.

As illustrated in FIG. 7A, the clamp 10A according to at least one embodiment of the present disclosure has the first inclined structure 48A formed on each side of the presser 40. The first inclined structure 48A includes a cutout portion 54 formed on each side of the presser 40. In the illustrated example, the cutout portion 54 is formed in a wedge-like, or triangular, shape; however, the shape is not limited thereto, and various shapes such as a rectangular shape or a semicircular shape can be adopted. In any event, the cutout portion 54 provides a space between the linear contact portion 40a (e.g., as shown in FIGS. 1-3) and a body of the presser 40. The first inclined structure 48A is not inclined in a state where the presser 40 does not overlie the sidewall 24.

The operation of the clamp 10A, configured as described above (e.g., with the one or more cutout portions 54, etc.), is described below.

As illustrated in FIG. 7B, when the clamp 10A is pressed in a state where the presser 40 overlies the sidewall 24, the first inclined structure 48A contacts the sidewall 24 thereby flexing the first inclined structure upward (e.g., in a direction toward the top of the movable portion 14), closing the space provided by the cutout portion 54. Then, in response to the space provided by cutout portion 54 being closed (e.g., where the cutout portion 54 is collapsed and flattened), the first inclined structure 48A deforms providing an inclined surface 54a that is formed on one or more side portions of the presser 40. The inclined surface 54a is inclined in such a direction that the dimension in the width direction of the presser 40 is decreased toward the lower end, and when the movable portion 14 is pressed toward the fixed portion 12, the presser 40 is guided between the pair of sidewalls 24 by the inclined surface 54a. In this manner, the first inclined structure 48A also functions as a structure that allows the presser 40 to be guided, or self-centered, between the pair of sidewalls 24.

In some embodiments, the clamp 10A of the present disclosure has the following effects.

The clamp 10A has, as the guide structure, the first inclined structure 48A that is formed in the presser 40 and generates, in the presser 40, an inclined surface 54a that is inclined toward the inside of the sidewall 24 when the presser 40 abuts on, or is forced into contact with, the upper end of the sidewall 24.

The clamp 10A also achieves the effect similar to that of the clamp 10 described above (e.g., the presser 40 is caused to self-center and be guided into the space between the sidewalls 24, etc.).

Note that, in the clamp 10A, the first inclined structure 48A is not limited to the cutout portion 54, and may be implemented by a member (e.g., flexure, spring, etc.) that generates an inclined surface as elastic compression proceeds more than other portions by applying a load that presses the presser 40 against the sidewall 24. For example, the first inclined structure 48A may be implemented by arranging an elastically compressible material on both sides of the presser 40.

Figure 8:
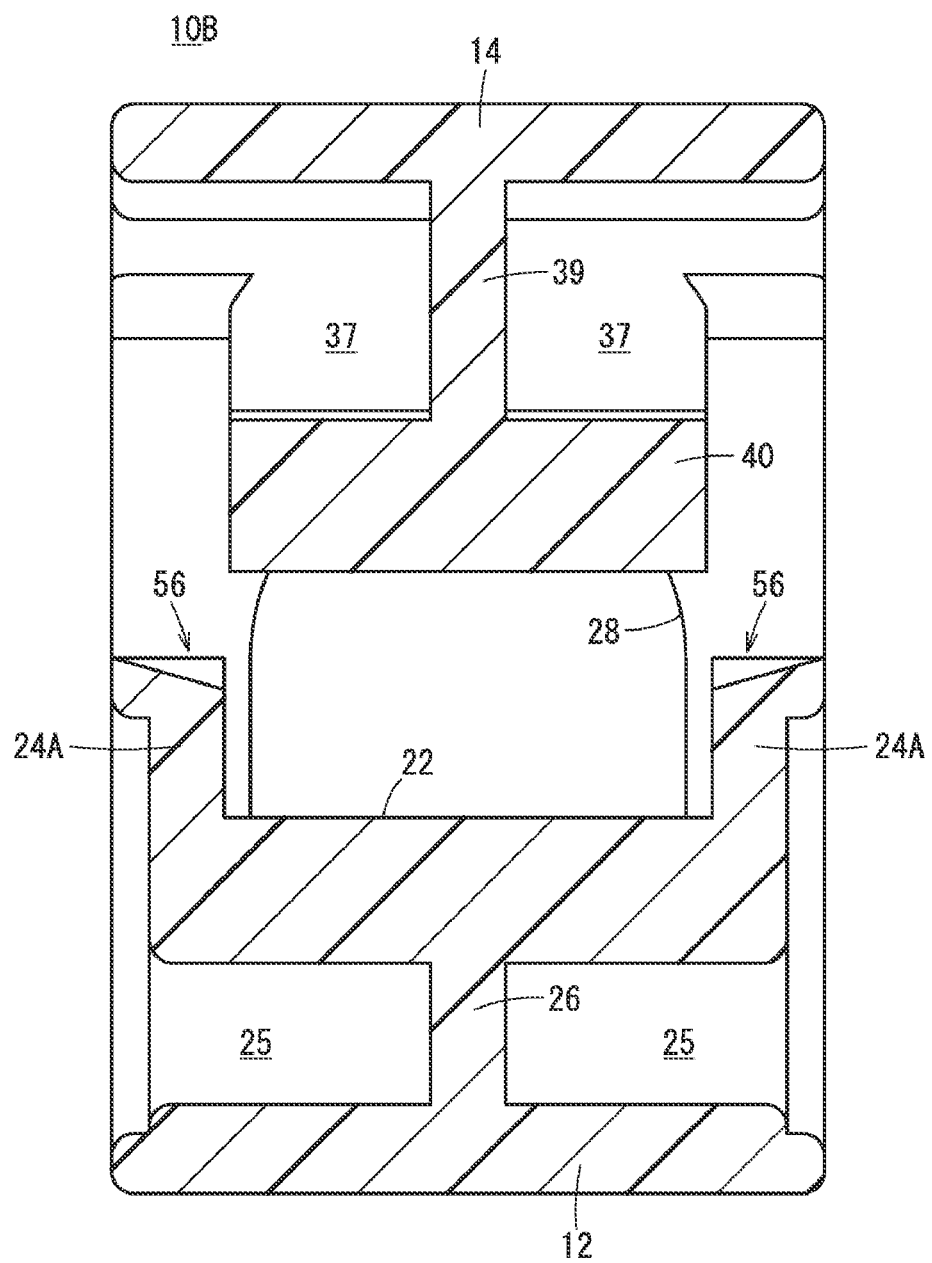
FIG. 8 illustrates a cross-sectional view of a clamp according to at least one embodiment of the present disclosure.

FIG. 8 illustrates a clamp 10B according to at least one embodiment of the present disclosure. In some embodiments, the clamp 10B includes a second inclined structure 56 arranged at the upper end of a sidewall 24A as a guide structure that allows the presser 40 to be guided between the sidewalls 24A. In the clamp 10B of the present disclosure, components similar, if not identical, to those of the clamp 10 according to the first embodiment are denoted by the same reference numerals, and the detailed description thereof is omitted.

In the clamp 10B, the second inclined structure 56 is provided at the upper end of the sidewall 24A instead of providing the inclined structure on each side of the presser 40. The second inclined structure 56 is inclined toward the inside of the pair of sidewalls 24A. To be specific, the second inclined structure 56 of the sidewall 24A on the left side in FIG. 8 is inclined downward from the side edge of the left end toward the inside (e.g., to the right side), and is an inclined surface that guides the side portion of the presser 40 toward the inside of the sidewall 24A. In addition, the second inclined structure 56 of the sidewall 24A on the right side is inclined downward from the side edge of the right end toward the inside (e.g., to the left side), and is an inclined surface that guides the presser 40 abutting on the sidewall 24A on the right side toward the inside of the sidewall 24A.

In some embodiments, the clamp 10B of the present disclosure has the following effects.

The clamp 10B has, as the guide structure, the second inclined structure 56 that is formed on the upper end of the sidewall 24A and is inclined toward the inside of the sidewall 24A.

According to the clamp 10B, even in a case where the presser 40 overlies the sidewall 24A, the second inclined structure 56 guides the presser 40 toward the inside of the sidewall 24A, so that the medical tube 80 can be reliably closed.

In the clamp 10B, the second inclined structure 56 is not limited to the flat surface, and may be implemented by a curve such as a spherical surface, an arcuate surface, and/or a paraboloid surface. Additionally or alternatively, the first inclined structure 48 may be formed on the presser 40 side.

Figure 9:
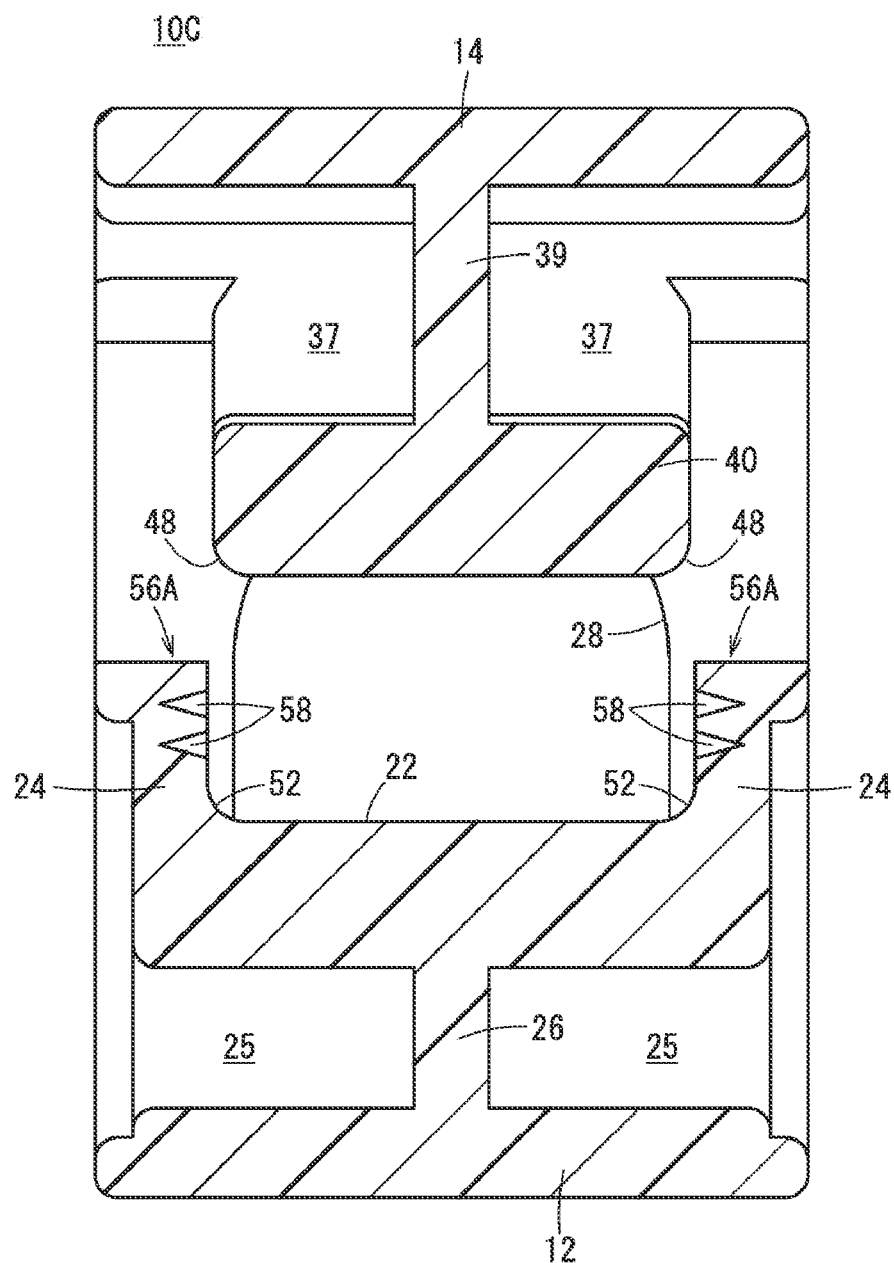
FIG. 9 illustrates a cross-sectional view of a clamp according to at least one embodiment of the present disclosure.

FIG. 9 illustrates a clamp 10C according to at least one embodiment of the present disclosure. The clamp 10C includes a second inclined structure 56A at the upper end of the sidewall 24 as the guide structure that allows the presser 40 to be guided between the sidewalls 24. In the clamp 10C of the present disclosure, components similar, or identical, to those of the clamp 10 described above are denoted by the same reference numerals, and the detailed description thereof is omitted.

The second inclined structure 56A of the clamp 10C has a cutout portion 58 formed in an inner portion of the sidewall 24. However, the upper end of the sidewall 24 is configured by a flat surface arranged substantially parallel to the bottom surface of the fixed portion 12 while not abutting on the presser 40. In the illustrated example, the first inclined structure 48 is formed on both sides of the presser 40; however, embodiments of the present disclosure are not limited thereto and it is possible that the first inclined structure 48 is not formed.

The operation of the clamp 10C, configured as described above (e.g., with the one or more cutout portions 58, etc.), is described below.

When the movable portion 14 of the clamp 10C is pressed and the presser 40 abuts on the upper end of the sidewall 24, the cutout portion 58 of the second inclined structure 56A may collapse (e.g., compress) and flatten due to a load applied from the upper end of the sidewall 24. As a result, the upper end of the sidewall 24 becomes an inclined surface inclined inward (e.g., toward a center of the clamp 10C). The inclined surface allows the presser 40 to be guided between the sidewalls 24. As described above, the second inclined structure 56A has a structure in which the inclined surface appears in response to the presser 40 abutting.

In some embodiments, the clamp 10C of the present disclosure has the following effects.

The clamp 10C has, as the guide structure, the second inclined structure 56A that is formed in the sidewall 24 and generates an inclined surface inclined inwardly (e.g., toward a center of the clamp 10C) in the upper end of the sidewall 24 in response to the presser 40 abutting.

According to the clamp 10C, even in a case where the presser 40 overlies the sidewall 24, the second inclined structure 56A guides the presser 40 toward the inside of the sidewall 24, so that the medical tube 80 can be reliably closed.

Figure 10B:
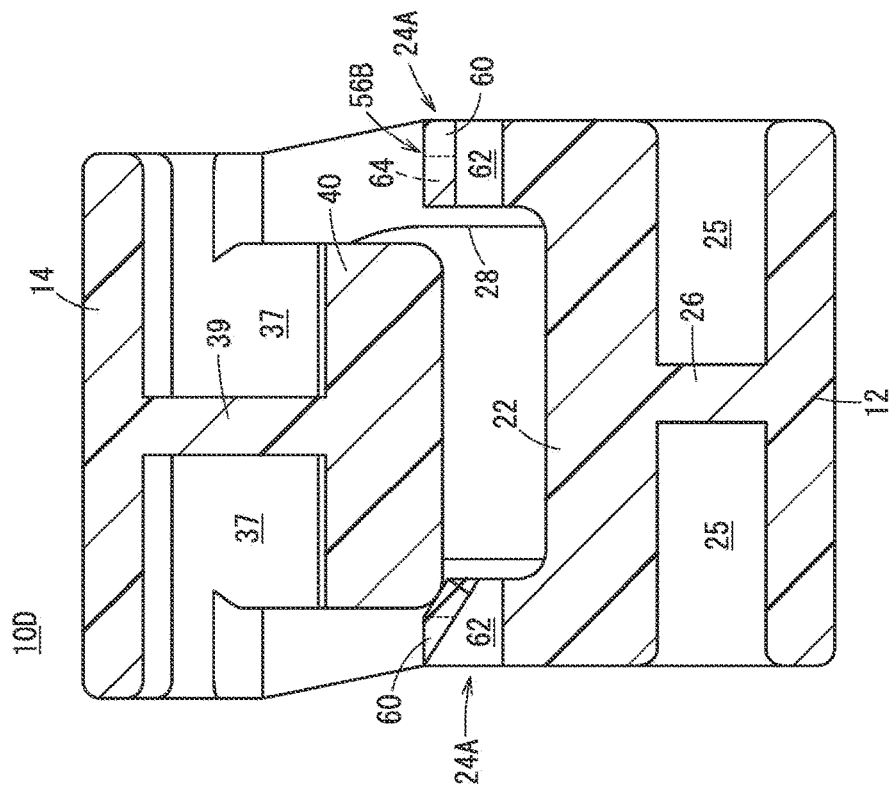
FIG. 10B is a cross-sectional view illustrating an operation for a case where a presser of the clamp of FIG. 10A overlies a sidewall.
Figure 10A:
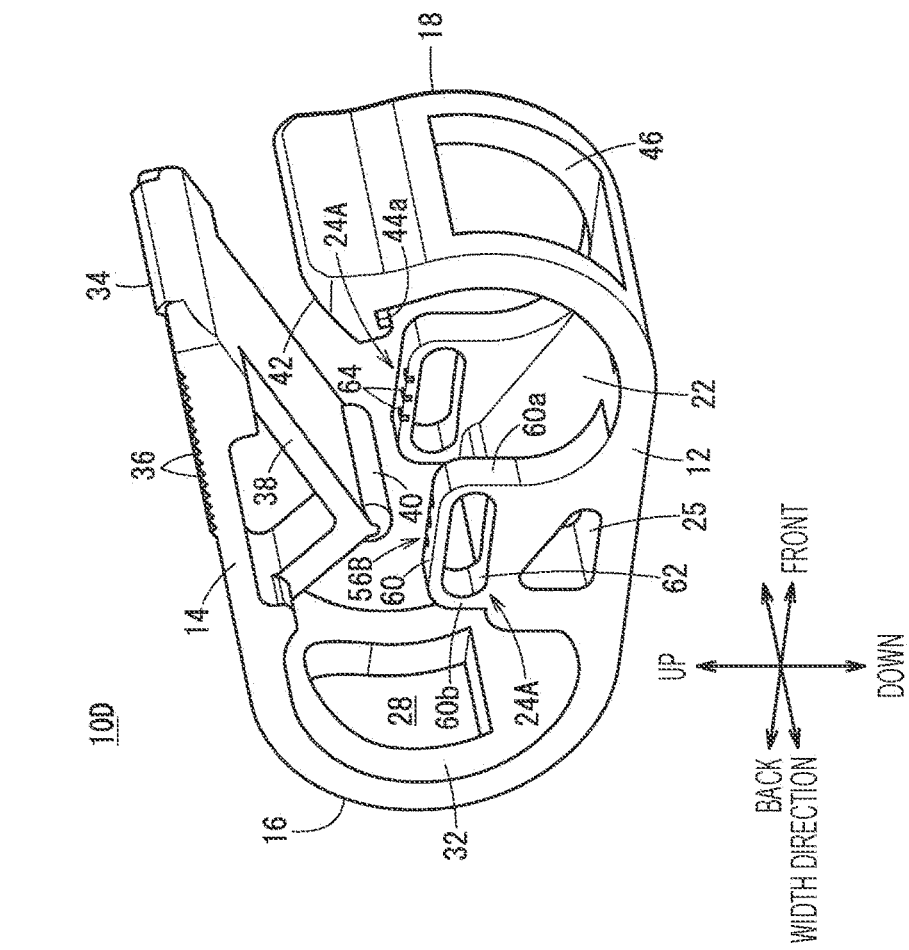
FIG. 10A illustrates a perspective view of a clamp according to at least one embodiment of the present disclosure.

FIG. 10A illustrates a clamp 10D, and the clamp 10D has a second inclined structure 56B disposed on the sidewall 24A as a guide structure that allows the presser 40 to be guided between the sidewalls 24A. In the clamp 10D, according to embodiments of the present disclosure, components similar, if not identical, to those of the clamp 10 according to the first embodiment are denoted by the same reference numerals, and the detailed description thereof is omitted.

The sidewall 24A of the clamp 10D is formed in a frame shape. The upper end of the sidewall 24A is configured by a plate member 60. The front end and the rear end of the plate member 60 are supported by support portions 60a and 60b. A hole 62 is provided below the plate member 60.

The second inclined structure 56B includes a plurality of cutout grooves 64 formed inside the plate member 60. The cutout grooves 64 are formed to a predetermined depth from the upper side toward the lower side of the plate member 60. Incidentally, the cutout grooves 64 may be formed to penetrate the plate member 60 in the up-down direction. Alternatively, the cutout grooves 64 may be formed so as to be cut from the lower side of the plate member 60 toward the upward direction.

The operation of the clamp 10D, configured as described above, is described below.

As illustrated in FIG. 10B, when the presser 40 overlies the upper end of the sidewall 24A, the plate member 60 is deformed about the cutout groove 64 due to a load applied from the presser 40. Since the cutout groove 64 is formed inside, the plate member 60 is deformed so as to be inclined inward as illustrated in FIG. 10B. Then, an inclined surface inclined inward is generated on the upper surface of the plate member 60. In this manner, the second inclined structure 56B forms an inclined surface that guides the presser 40 inward when the presser 40 overlies the sidewall 24A. As a result, in the clamp 10D, the presser 40 is guided between the sidewalls 24A, so that the medical tube 80 can be reliably closed.

Although the present disclosure has been described above with reference to preferred embodiments, the present disclosure is not limited to the above embodiments, and it goes without saying that various modifications can be made without departing from the gist of the present disclosure.

References in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in conjunction with one embodiment, it is submitted that the description of such feature, structure, or characteristic may apply to any other embodiment unless so stated and/or except as will be readily apparent to one skilled in the art from the description. The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

It is to be appreciated that any feature described herein can be claimed in combination with any other feature(s) as described herein, regardless of whether the features come from the same described embodiment.

As used herein, the singular forms "a," "an," and "the" are intended to include the plural forms as well, unless the context clearly indicates otherwise. It will be further understood that the terms "include," "including," "includes," "comprise," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B, and C together. When each one of A, B, and C in the above expressions refers to an element, such as X, Y, and Z, or a class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

What is claimed is:

1. A clamp, comprising:
   a fixed portion on which a tube is placed;
   a movable portion that is arranged above the fixed portion, wherein the movable portion faces the fixed portion; and
   a closing portion configured to press and close the tube in response to the movable portion being pressed in a direction toward the fixed portion, wherein the closing portion comprises:
      a presser that protrudes from the movable portion toward the fixed portion and presses the tube;
      a pair of sidewalls that extend in a wall shape from sides of the fixed portion and prevent the tube from being shifted laterally; and
      a guide structure that is arranged in at least one of the presser and in at least one sidewall of the pair of sidewalls, wherein the guide structure guides the presser between the pair of sidewalls, wherein the guide structure includes a first inclined structure that is formed in a side of the presser and is inclined toward a space arranged between the pair of sidewalls, wherein the first inclined structure has a spherical surface, and wherein a raised portion corresponding to a shape of the first inclined structure is formed at a boundary between the fixed portion and the pair of sidewalls.

2. The clamp according to claim 1, wherein the raised portion is formed over an entire region of the pair of sidewalls along an extending longitudinal direction of the tube.

3. The clamp according to claim 1, wherein the guide structure includes a second inclined structure that is formed in the at least one sidewall of the pair of sidewalls and forms, in an upper end of the at least one sidewall of the pair of sidewalls, an inclined surface inclined inwardly toward a center of the clamp in response to the presser contacting the at least one sidewall of the pair of sidewalls.

4. A clamp, comprising:
   a fixed portion comprising:
      a pair of sidewalls extending from the fixed portion in a first direction to an upper surface of the pair of sidewalls; and
      a tube contact surface arranged in a space between the pair of sidewalls, the tube contact surface disposed below the upper surface;
   a movable portion hingedly attached to the fixed portion at a first end of the fixed portion, wherein the movable portion is movable between an open state and a closed state, and wherein the movable portion comprises:
      a protrusion extending in a direction toward the fixed portion, wherein the protrusion terminates at a peak arranged at a point offset from the movable portion; and a presser arranged at the peak of the protrusion, the presser formed having a columnar shape; and a guide structure that is arranged in at least one of the presser and in at least one sidewall of the pair of sidewalls, wherein the guide structure guides the presser between the pair of sidewalls when the movable portion moves between the open state and the closed state, wherein the guide structure is formed as at least one radiused end of the presser comprising a surface radius size, wherein a fillet is disposed between the tube contact surface and each sidewall of the pair of sidewalls, and wherein the fillet comprises the surface radius size, wherein, in the open state, the movable portion is arranged spaced apart a first distance from the fixed portion such that the movable portion is disposed apart from the fixed portion at a second end of the fixed portion opposite the first end, wherein, in the closed state, the movable portion is arranged a second distance from the fixed portion such that the movable portion is disposed in contact with the fixed portion at the second end, and wherein the second distance is smaller than the first distance.

5. The clamp of claim 4, wherein, as the movable portion is moved from the open state to the closed state, the radiused end of the presser contacts at least one sidewall of the pair of sidewalls at the upper surface guiding the presser into the space between the pair of sidewalls.

6. The clamp of claim 4, wherein the tube contact surface is arranged as a flat surface extending along a length and a width of the clamp.

7. The clamp of claim 4, wherein the columnar shape of the presser is cylindrical, and wherein a linear contact portion of the presser is arranged along a width of the movable portion.

8. The clamp of claim 4, further comprising:
a curved portion extending from the first end of the fixed portion in a direction away from the fixed portion, wherein the movable portion is interconnected to the curved portion, and wherein the curved portion corresponds to a living hinge of the clamp.

9. The clamp of claim 8, further comprising:
an upright portion extending from the second end of the fixed portion in the direction away from the fixed portion, wherein the upright portion comprises a groove lock extending across a width of the upright portion.

10. The clamp of claim 9, wherein the movable portion comprises a claw protrusion extending across a width of the movable portion, and wherein, in the closed state, the claw protrusion is engaged with the groove lock of the upright portion.

11. The clamp of claim 10, further comprising:
a first aperture passing through the curved portion;
a second aperture passing through the upright portion; and
a tube receiving space extending from the first aperture to the second aperture, the tube receiving space being disposed between the fixed portion and the movable portion.

12. A clamp, comprising:
a fixed portion configured to engage with a tube;
a movable portion interconnected to the fixed portion, the movable portion arranged above the fixed portion and comprising a surface that faces the fixed portion; and
a closing portion configured to move between an open state and a closed state, wherein, in the open state, the tube is capable of moving relative to the clamp, wherein, in the closed state, the tube is pressed and closed by the clamp, and wherein the closing portion comprises:
a presser that protrudes from the movable portion toward the fixed portion;
a pair of sidewalls that extend in a wall shape from opposite sides of the fixed portion and defines a tube receiving space of the clamp; and
a guide structure that is arranged in at least one of the presser and in at least one sidewall of the pair of sidewalls, wherein the guide structure centers the movable portion relative to the fixed portion when moved from the open state to the closed state, wherein the guide structure includes a first inclined structure that is formed in a side of the presser and is inclined toward the tube receiving space, wherein the first inclined structure has a spherical surface, and wherein a raised portion corresponding to a shape of the first inclined structure is formed at a boundary between the fixed portion and the pair of sidewalls.

* * * * *